(12) United States Patent
Spencer et al.

(10) Patent No.: US 10,342,457 B2
(45) Date of Patent: Jul. 9, 2019

(54) METHOD AND SYSTEM FOR MONITORING THE LUNG FUNCTION OF A PATIENT (71) Applicant: KONINKLIJKE PHILIPS N.V., Eindhoven (NL)

(72) Inventors: Timothy Spencer, Chichester (GB); Anthony Dyche, Hayling Island (GB); Ian Philip Rabbetts, Hayling Island (GB)

(73) Assignee: KONINJKLIJKE PHILIPS N.V., Eindhoven (NL)

( * ) Notice: Subject to any disclaimer, the term of this patent is extended or adjusted under 35 U.S.C. 154(b) by 744 days.

(21) Appl. No.: 14/399,314

(22) PCT Filed: May 28, 2013

(86) PCT No.: PCT/IB2013/054389
§ 371 (c)(1),
(2) Date: Nov. 6, 2014

(87) PCT Pub. No.: WO2013/182951
PCT Pub. Date: Dec. 12, 2013

(65) Prior Publication Data
US 2015/0099994 A1    Apr. 9, 2015

Related U.S. Application Data

(60) Provisional application No. 61/657,062, filed on Jun. 8, 2012.

(51) Int. Cl.
*A61B 5/087*    (2006.01)
*A61M 15/00*   (2006.01)
(Continued)

(52) U.S. Cl.
CPC ............... *A61B 5/087* (2013.01); *A61B 5/085* (2013.01); *A61B 5/097* (2013.01); *A61B 5/4842* (2013.01);
(Continued)

(58) Field of Classification Search
CPC ....... A61B 5/085; A61B 5/097; A61B 5/7275; A61B 5/4842; A61B 5/7246; A61B 5/087;
(Continued)

(56) References Cited

U.S. PATENT DOCUMENTS 5,404,871 A * 4/1995 Goodman ............. A61M 15/00
                                                                128/200.14
5,450,336 A     9/1995 Rubsamen et al.
(Continued)

FOREIGN PATENT DOCUMENTS

EP    2245985 A1    11/2010
GB    2395437 A      5/2004
(Continued)

OTHER PUBLICATIONS

Zou et al, "Receiver-Operating Characteristic Analysis for Evaluating Diagnostic Test and Predictive Models", Circulation, vol. 115, 2007, p. 654-657.
(Continued)

*Primary Examiner* — Meredith Weare
(74) *Attorney, Agent, or Firm* — Michael W. Haas (57) ABSTRACT

There is provided a method of monitoring the lung function of a patient, the method comprising determining one or both of an inhalation time and a rest time for a patient that is using a respiratory apparatus, the one or both of an inhalation time and a rest time for the patient being determined from measurements obtained from the respiratory apparatus, wherein the inhalation time is the amount of time for which
(Continued)

the patient inhales through the respiratory apparatus, and the rest time is the amount of time between the end of an exhalation and the start of the next inhalation; and analyzing the determined one or both of the inhalation time and rest time to determine an indication of the lung function of the patient.

10 Claims, 3 Drawing Sheets

(51) Int. Cl.
  *A61B 5/085* (2006.01)
  *A61B 5/097* (2006.01)
  *A61B 5/00* (2006.01)
  *A61M 16/00* (2006.01)
(52) U.S. Cl.
  CPC .......... *A61B 5/7246* (2013.01); *A61B 5/7275* (2013.01); *A61M 15/008* (2014.02); *A61M 15/0085* (2013.01); *A61M 2016/0039* (2013.01); *A61M 2205/3569* (2013.01); *A61M 2205/3592* (2013.01); *A61M 2205/502* (2013.01)
(58) Field of Classification Search
  CPC ............ A61M 15/008; A61M 15/0085; A61M 2016/0039; A61M 2205/3569; A61M 2205/3592; A61M 2205/502
  See application file for complete search history.

(56) References Cited

U.S. PATENT DOCUMENTS

| | | | | |
|---|---|---|---|---|
| 5,469,750 | A * | 11/1995 | Lloyd | A61M 15/00 73/1.34 |
| 5,608,647 | A * | 3/1997 | Rubsamen | A61M 15/0091 128/204.18 |
| 5,800,337 | A | 9/1998 | Gabish | |
| 6,015,388 | A * | 1/2000 | Sackner | A61B 5/08 600/529 |
| 6,224,560 | B1 * | 5/2001 | Gazula | A61B 5/087 128/204.23 |
| 7,314,451 | B2 | 1/2008 | Halperin et al. | |
| 7,575,553 | B2 | 8/2009 | Stahmann et al. | |
| 7,748,382 | B2 * | 7/2010 | Denyer | A61M 15/0085 128/200.24 |
| 7,973,005 | B2 | 7/2011 | Bauer | |
| 8,875,697 | B2 * | 11/2014 | Denyer | A61M 15/00 128/200.16 |
| 2004/0039295 | A1 * | 2/2004 | Olbrich | A61B 5/0205 600/538 |
| 2006/0237001 | A1 | 10/2006 | Stangl | |
| 2006/0243277 | A1 * | 11/2006 | Denyer | A61M 15/0085 128/202.22 |
| 2006/0253045 | A1 * | 11/2006 | Coifman | A61B 5/0871 600/538 |
| 2007/0191688 | A1 * | 8/2007 | Lynn | A61B 5/412 600/300 |
| 2007/0293779 | A1 * | 12/2007 | Bardy | A61B 5/0031 600/529 |
| 2008/0047553 | A1 * | 2/2008 | Denyer | A61M 15/008 128/203.12 |
| 2009/0025714 | A1 * | 1/2009 | Denyer | A61M 15/00 128/200.23 |
| 2010/0249633 | A1 * | 9/2010 | Droitcour | A61B 5/05 600/534 |
| 2011/0004081 | A1 | 1/2011 | Addison et al. | |
| 2011/0105936 | A1 * | 5/2011 | Addington | A61M 11/02 600/534 |
| 2011/0112442 | A1 | 5/2011 | Meger et al. | |
| 2011/0121462 | A1 | 5/2011 | Kim | |
| 2012/0041279 | A1 | 2/2012 | Freeman et al. | |
| 2013/0156158 | A1 | 6/2013 | Noji et al. | |

FOREIGN PATENT DOCUMENTS

| | | |
|---|---|---|
| WO | 2004019041 A1 | 3/2004 |
| WO | 2007140508 A1 | 12/2007 |
| WO | 2012026146 A1 | 3/2012 |

OTHER PUBLICATIONS

Van Devanter et al, "Pulmonary Outcome Prediction (POP) Tools for Cystic Fibrosis Patients", Pediatric Pulmonolgy, vol. 45, 2010, p. 1156-1166.

Kraemer, "Pulmonary Outcome Predicition for Cystic Fibrosis Patients", Pediatric Pulmonology, vol. 45, Issue 12, pp. 1153-1155, Dec. 2010.

McFadden et al, "Improper Patient Techniques With Metered Dose Inhales: Clinical Consequences and Solutions to Misuse", Journal of Allergy and Clinical Immunology, vol. 96, No. 2, Aug. 1, 1995, p. 278-283.

Parkes, M.J., "Breath-holding and its breakpoint: Breath-holding and its breakpoint", Experimental Physiology, vol. 1, No. 1, Dec. 20, 2005, pp. 1-15.

* cited by examiner

METHOD AND SYSTEM FOR MONITORING THE LUNG FUNCTION OF A PATIENT

CROSS-REFERENCE TO PRIOR APPLICATIONS

This application is the U.S. National Phase application under 35 U.S.C. § 371 of International Application No. PCT/IB2013/054389, filed on May 28, 2013, which claims the benefit of U.S. Provisional Patent Application No. 61/657,062 filed on Jun. 8, 2012. These applications are hereby incorporated by reference herein.

TECHNICAL FIELD OF THE INVENTION

The invention relates to a method and system for monitoring the health of a patient, and in particular relates to a method and system for determining an indication of the lung function of the patient.

BACKGROUND TO THE INVENTION

The loss or reduction in lung function in patients with cystic fibrosis (CF) is associated with increased mortality and varies between individuals and over time. The management of these patients would be improved if lung function decline or imminent pulmonary exacerbations could be predicted or detected at an early stage. The number and severity of pulmonary exacerbations influence the final outcome of the disease by speeding up the overall deterioration of the patient. Exacerbations are defined by acute onset of pulmonary symptoms such as breathlessness, increased coughing, changes in the color of sputum and loss of appetite and weight. Detection of the acute onset of these pre-clinical symptoms would avoid costly and unnecessary hospitalization for intravenous (IV) antibiotic therapy by allowing timely non-emergency intervention by the clinician or other healthcare professional.

Several techniques have been published which purport to aid the clinician in assessing the pulmonary status of patients with cystic fibrosis, often involving spirometry parameters and chest x-ray scores. In the case of "Pulmonary Outcome Prediction for Cystic Fibrosis Patients" by Kraemer, R. and Thamrin, C. *Pediatr Pulmonol* 45: 1153-1155, 2010 a complex, composite score is derived from retrospective data. Some techniques, such as that shown in EP 2245985, involve the use of specific respiratory equipment, primarily for use with patients with Chronic Obstructive Pulmonary Disease (COPD). Other more general techniques for the monitoring of clinical episodes have been described which involve measuring a number of physiological parameters and various biological markers have been identified that could be used for detecting exacerbations.

Given that patients with cystic fibrosis may infrequently visit clinics and have long periods in which they self-manage their condition whilst leading normal active lives, exacerbation detection techniques cannot rely on 'old' data taken during previous clinical visits, neither can they wait until the next routine hospital visit.

Therefore, there is a need for an improved method and system for determining an indication of the lung function of the patient. In particular, it is desirable to be able to derive the indication of the lung function from parameters that are obtainable from apparatus that can used in the home environment of a patient. It is also desirable to provide an early indication of when the lung function of the patient is deteriorating.

SUMMARY OF THE INVENTION

Self-management of a condition such as cystic fibrosis can include the regular use of a respiratory apparatus, such as a nebulizer, that is used to deliver medication to the patient. In some cases, a patient using such an apparatus can be required to complete a series of defined breathing manoeuvres, such as long, slow inhalations (which are desirable as they improve the efficiency of the treatment).

However, patients with poor lung function may be unable to inhale for the required amount of time, and may require frequent and relatively long rest periods between exhaling and starting a subsequent inhalation. Therefore, it has been realized that a good indicator of the lung function of the patient can be given by the amount of time, proportionally, that the patient inhales during use of the apparatus and/or the amount of time that the patient has to rest between an exhalation and the start of the next inhalation.

Thus, according to a first aspect of the invention, there is provided a method of monitoring the lung function of a patient, the method comprising determining one or both of an inhalation time and a rest time for a patient that is using a respiratory apparatus, the one or both of an inhalation time and a rest time for the patient being determined from measurements obtained from the respiratory apparatus, wherein the inhalation time is the amount of time for which the patient inhales through the respiratory apparatus, and the rest time is the amount of time between the end of an exhalation and the start of the next inhalation; and analyzing the determined one or both of the inhalation time and rest time to determine an indication of the lung function of the patient.

Preferably, the step of determining one or both of an inhalation time and a rest time comprises measuring the air flow through the respiratory apparatus as the patient inhales and exhales through the respiratory apparatus, and determining the one or both of the inhalation time and rest time from the times where the direction of the air flow through the respiratory apparatus changes. This means that the invention can be integrated into an existing respiratory apparatus, such as a nebulizer, used by a patient, it is not necessary for the patient to use a separate apparatus to provide the indication of their lung function.

In some embodiments, the patient can be required to inhale through the respiratory apparatus for a target inhalation time. The target inhalation time can be constant, or it can be increased for a subsequent inhalation by the patient if the patient inhales for a time equal to or exceeding the target inhalation time.

In a preferred embodiment, the step of analyzing the determined one or both of the inhalation time and rest time to determine an indication of the lung function of the patient comprises determining a ratio of the inhalation time to the rest time.

In a further preferred embodiment, the step of analyzing the determined one or both of the inhalation time and rest time to determine an indication of the lung function of the patient comprises determining a ratio of the rest time and the total amount of time that the respiratory apparatus is in use by the patient.

The inhalation time can be one or more of: the amount of time for which the patient inhales through the respiratory apparatus in a single breath, the average amount of time for which the patient inhales through the respiratory apparatus over a plurality of breaths, and the total amount of time that the patient is inhaling through the respiratory apparatus over a plurality of breaths. Likewise, the rest time can be one or more of: the amount of time between the end of an exhalation and the start of the next inhalation for a single breath, the average amount of time between the end of an exhalation and the start of the next inhalation over a plurality of breaths, and the total amount of time between the end of an exhalation and the start of the next inhalation over a plurality of breaths.

Preferably, the step of analyzing the determined one or both of the inhalation time and rest time to determine an indication of the lung function of the patient further comprises comparing the determined indication to one or more thresholds.

Preferably, the step of analyzing the determined one or both of the inhalation time and rest time to determine an indication of the lung function of the patient further comprises comparing the determined indication to one or more earlier determined indications of the lung function of the patient to determine a change in the lung function of the patient. In this way, it is possible to evaluate the lung function of the patient over time and to help anticipate periods where the patient's lung function is likely to be significantly impaired. Preferably, the determined change in the lung function of the patient is compared to one or more thresholds.

The step of analyzing can further comprise determining the rate of change in the lung function of the patient. Preferably, the determined rate of change in the lung function of the patient is compared to one or more thresholds.

According to a second aspect of the invention, there is provided a computer program product comprising computer readable code, the computer readable code being arranged such that, on execution of the code by a suitable computer or processor, the computer or processor is configured to perform any of the methods described above.

According to a third aspect of the invention, there is provided a system for use in monitoring the lung function of a patient, the system comprising a processing unit configured to obtain measurements of one or both of an inhalation time and a rest time for a patient that is using a respiratory apparatus, wherein the inhalation time is the amount of time for which the patient inhales through the respiratory apparatus, and the rest time is the amount of time between the end of an exhalation and the start of the next inhalation; and to analyses the determined one or both of the inhalation time and rest time to determine an indication of the lung function of the patient.

The system can further comprise a respiratory apparatus through which the patient is to inhale and exhale, the respiratory apparatus being configured to obtain measurements for use by the processing unit in determining the one or both of an inhalation time and a rest time for the patient.

In some embodiments, the processing unit is part of the respiratory apparatus. In alternative embodiments, the processing unit is separate from the respiratory apparatus.

Preferably, the measurements of one or both of an inhalation time and a rest time are obtained by a sensor that measures the air flow through the respiratory apparatus as the patient inhales and exhales through the respiratory apparatus, and the processor is configured to determine the measurements of the one or both of the inhalation time and rest time from the times where the direction of the air flow through the respiratory apparatus changes.

In some embodiments, the respiratory apparatus can be configured to operate in a Target Inhalation Mode in which the patient is required or encouraged to inhale for a target inhalation time. The target inhalation time can be constant, or it can be increased for a subsequent inhalation by the patient if the patient inhales for a time equal to or exceeding the target inhalation time.

In a preferred embodiment, the processor is configured to analyses the determined one or both of the inhalation time and rest time to determine an indication of the lung function of the patient by determining a ratio of the inhalation time to the rest time.

In a further preferred embodiment, the processor is configured to analyses the determined one or both of the inhalation time and rest time to determine an indication of the lung function of the patient by determining a ratio of the rest time and the total amount of time that the respiratory apparatus is in use by the patient.

The inhalation time can be one or more of: the amount of time for which the patient inhales through the respiratory apparatus in a single breath, the average amount of time for which the patient inhales through the respiratory apparatus over a plurality of breaths, and the total amount of time that the patient is inhaling through the respiratory apparatus over a plurality of breaths. Likewise, the rest time can be one or more of: the amount of time between the end of an exhalation and the start of the next inhalation for a single breath, the average amount of time between the end of an exhalation and the start of the next inhalation over a plurality of breaths, and the total amount of time between the end of an exhalation and the start of the next inhalation over a plurality of breaths.

Preferably, the processor is configured to analyses the determined one or both of the inhalation time and rest time to determine an indication of the lung function of the patient further by comparing the determined indication to one or more thresholds.

Preferably, the processor is configured to analyses the determined one or both of the inhalation time and rest time to determine an indication of the lung function of the patient by comparing the determined indication to one or more earlier determined indications of the lung function of the patient to determine a change in the lung function of the patient. In this way, it is possible to evaluate the lung function of the patient over time and to help anticipate periods where the patient's lung function is likely to be significantly impaired. Preferably, the determined change in the lung function of the patient is compared to one or more thresholds.

The processor can be further configured to determine the rate of change in the lung function of the patient. Preferably, the determined rate of change in the lung function of the patient is compared to one or more thresholds.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
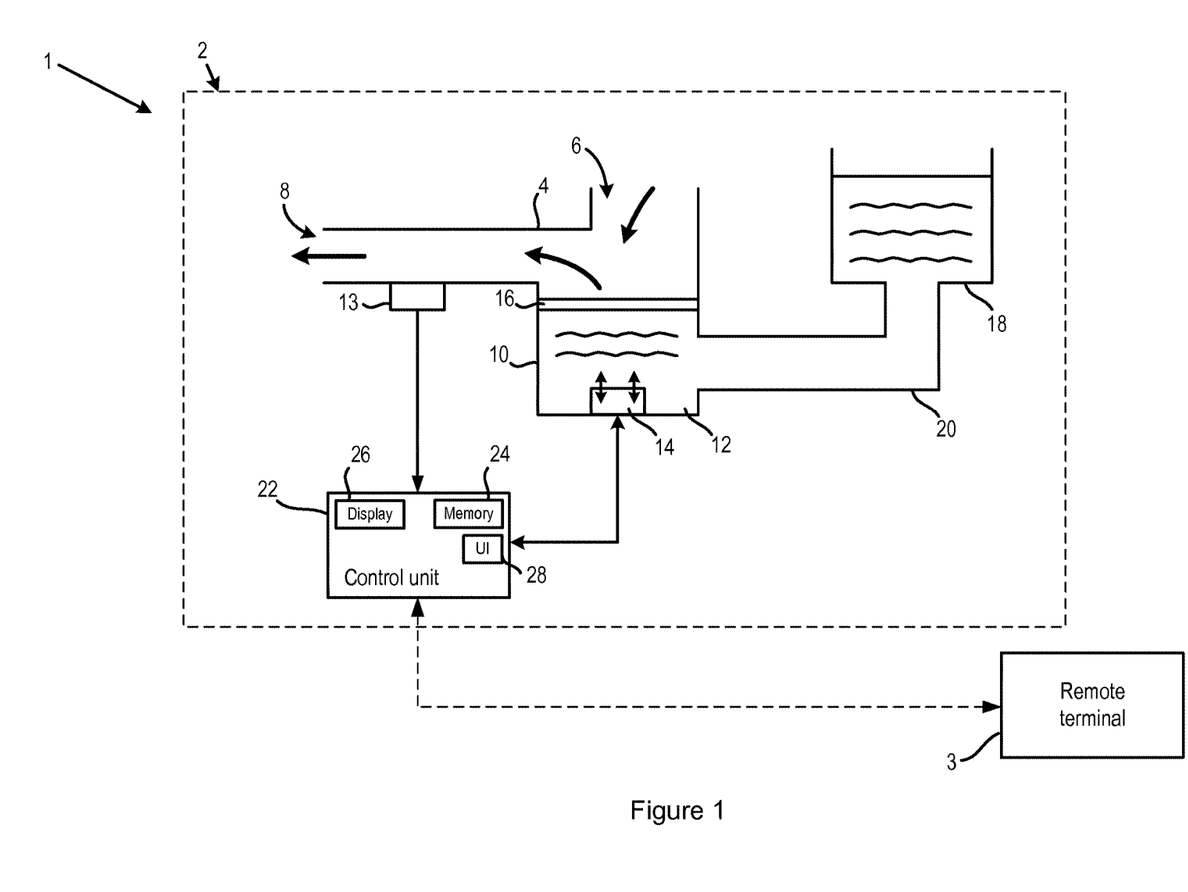
FIG. 1 is an illustration of a system according to an embodiment of the invention.

FIG. 1 shows an exemplary system 1 according to an embodiment of the invention. The system comprises a nebulizer 2 that is used to administer a medication to a patient according to a treatment plan, and a remote terminal 3 that can be selectively connected to the nebulizer 2 to receive data on the breathing performance of the patient while using the nebulizer 2.

The nebulizer 2 shown in FIG. 1 is a piezo-mesh based nebulizer which is commonly used to generate aerosols in a drug delivery apparatus. In these types of nebulizers 2, a piezoelectric element vibrates a nozzle plate (also referred to as a mesh) to produce the fine aerosol spray.

The nebulizer 2 comprises a body or housing 4 having an inlet 6 and an outlet 8 arranged so that when a user of the nebulizer 2 inhales through the outlet 8, air is drawn into and through the nebulizer 2 via the inlet 6 and outlet 8 and into the user's body. The outlet 8 is typically provided in the form of a mouthpiece or a facial or nasal mask or in a form that is suitable for connection to a separate replaceable mouthpiece or facial or nasal mask. The housing 4, inlet 6 and outlet 8 are also arranged so that the user can exhale through the nebulizer 2.

The nebulizer 2 comprises a nebulizing chamber 10 located between the inlet 6 and outlet 8 that holds a liquid 12, for example a medication or drug, that is to be nebulized (i.e. to be turned into a fine mist or spray). The nebulizer 2 is configured such that fine droplets of the nebulized liquid 12 combine with the air drawn through the nebulizer 2 when the user inhales to deliver a dose of the medication or drug to the user.

An air flow sensor 13 is arranged in the nebulizer 2 that detects the direction in which air is flowing through the housing 4. The air flow sensor 13 may also be configured to measure the speed of the air too. The information from the air flow sensor 13 can be used to determine when the user is inhaling and exhaling. The signal output from the air flow sensor 13 can be an analog or digital signal indicating the direction and magnitude of the air flow in the vicinity of the sensor 13. In alternative embodiments, the air flow sensor 13 can be replaced with an air pressure sensor or any other type of sensor that can detect the direction of air flow through the nebulizer 2.

An actuator 14 is provided for agitating or vibrating the liquid 12 held in the nebulizing chamber 10. The actuator 14 is typically provided in the form of a piezoelectric element, although those skilled in the art will appreciate that other forms of actuator 14 can be used. The piezoelectric element 14 can be covered with a plastic or metal cover layer to avoid direct contact between the piezoelectric element and the liquid 12 (although alternative types of material can be used for the cover layer).

A nozzle plate 16 is provided in the nebulizing chamber 10 for nebulizing the liquid 12 when the liquid 12 is vibrated by the actuator 14. The nozzle plate 16 is typically in the form of a mesh or membrane having a plurality of small holes or nozzles through which small amounts of the liquid can pass. The size (diameter) of the nozzles in the nozzle plate 16 determines, among other things, the size of the droplets of liquid produced when the nebulizer 2 is activated. In some embodiments, the nozzle plate 16 is removable from the nebulizer 2 so that it can be cleaned or completely replaced, as required.

In FIG. 1, the actuator 14 is separate from the nozzle plate 16 and is positioned at, or proximate to, the bottom of the nebulizing chamber 10 in order to agitate the liquid 12, although alternatively the actuator 14 can be in contact with or integral with the nozzle plate 16 and can vibrate the nozzle plate 16 in order to nebulize the liquid 12.

In use, the liquid 12 fills the nebulizing chamber 10 up to the height of the nozzle plate 16. It will be appreciated that the liquid 12 in the nebulizing chamber 10 will be depleted as the nebulizer 2 is operated, and more liquid 12 must be added to the nebulizing chamber 10 to maintain the liquid 12 at the required height for the nebulizer 2 to continue operating. Therefore, the nebulizer 2 comprises a metering or reservoir chamber 18 that stores liquid for replenishing the liquid 12 in the nebulizing chamber 10. The liquid from the metering chamber 18 may flow into the nebulizing chamber 10 through a connecting tube 20 due to the action of gravity and/or capillary filling.

The metering chamber 18 holds the total volume of liquid 12 that is to be nebulized during a single use of the nebulizer 2.

The nebulizer 2 further comprises a control unit 22 that controls the operation of the nebulizer 2. The control unit 22 is electrically connected to the air flow sensor 13 and the actuator 14. When the control unit 22 determines from the information received from the air flow sensor 13 that the user is inhaling, the control unit 22 outputs control signals to the actuator 14 to cause the actuator 14 to operate (vibrate) and thereby nebulize the liquid 12 by vibrating or pushing the liquid 12 through the nozzle plate 16. When the control unit 22 determines from the information received from the air flow sensor 13 that the user has stopped inhaling, the control unit 22 can cease the operation (vibration) of the actuator 14. This on/off operation of the actuator 14 continues until the required amount of liquid 12 has been nebulized.

The control unit 22 comprises a memory module 24 for storing operating parameters and/or program instructions for use by the control unit 22 during operation of the nebulizer 2. The operating parameters may, for example, relate to the treatment regimen to be provided by the nebulizer 2, such as the required treatment time, required treatment volume (dosage) and/or medication flow rate (i.e. the volume of liquid to be nebulized per unit time). The memory module 24 can also store measurements from the air flow sensor 13 for subsequent processing to determine the lung function of the patient according to the invention, and information on the previous use or uses of the nebulizer 2 by the patient (either or both of the measurements from the air flow sensor 13 from the previous use or uses and indications of the lung function of the patient derived from those previous measurements).

The control unit 22 can further comprise a display 26 for displaying information on the status of the nebulizer 2 and the patient to the patient and a user interface 28 to allow the patient to activate the nebulizer 2. Such a display 26 might comprise an LCD screen or other suitable type of display, or one or more LEDs or lights. The display 26 can present information indicating, for example, whether the nebulizer 2 is ready for use and the dosage time and/or amount remaining.

The user interface 28 allows the user to operate the nebulizer 2. The user interface can comprise a single button, switch or other input means (such as a touch screen) that can be used for powering on or otherwise activating the nebulizer 2, or multiple buttons or other input means that allow the user to select various settings or options for the nebulizer 2.

Although a piezo-mesh based nebulizer is shown in FIG. 1, it will be appreciated by those skilled in the art that the invention is not limited to any particular type of nebulizer, and nebulizers having different arrangements or modes of operation to that shown in FIG. 1 can be used to provide the indication of lung function according to the invention. Moreover, it will be appreciated that the invention is not limited to use with nebulizers, and the invention can be implemented in any type of respiratory apparatus that requires the patient (user) to perform a number of breaths therethrough and in which an inhalation period and/or rest period can be measured.

The nebulizer 2 can be connected to the remote terminal 3 by the patient using wired or wireless means and the information stored in the memory module 24 can be uploaded to the remote terminal 3. In particular, the nebulizer 2 can transmit the stored measurements from the air flow sensor 13 and/or indications of the lung function of the patient (if the control unit 22 has performed the required processing) to the remote terminal 3. The remote terminal 3 can analyses the measurements to determine an indication of the current lung function of the patient in accordance with the invention, and optionally the change in the lung function over time, and, if required (for example if it is found that the patient's lung function is deteriorating or is likely to deteriorate significantly), issue an alert to the patient that they need to adjust their medication dosage, visit their healthcare professional or perhaps obtain emergency assistance.

The remote terminal 3 can be a dedicated base unit (including, for example, a charging dock) for the nebulizer 2 that is located in the home of the patient or a computing device belonging to the patient, such as a mobile telephone, smart phone, PDA, laptop or desktop computer. In these cases, the remote terminal 3 can be configured to transmit the indication of the lung function of the patient to a server or computer of a healthcare professional, so that the healthcare professional can review the information and take appropriate clinical decisions. Such transmission can include transmission via a telecommunication network and/or the Internet. In alternative embodiments, the remote terminal 3 can comprise a server or computer of a healthcare professional, in which case the nebulizer 2 can be configured to transmit the information stored in the memory module 24 via a telecommunication network and/or the Internet to the remote terminal 3.

Figure 2:
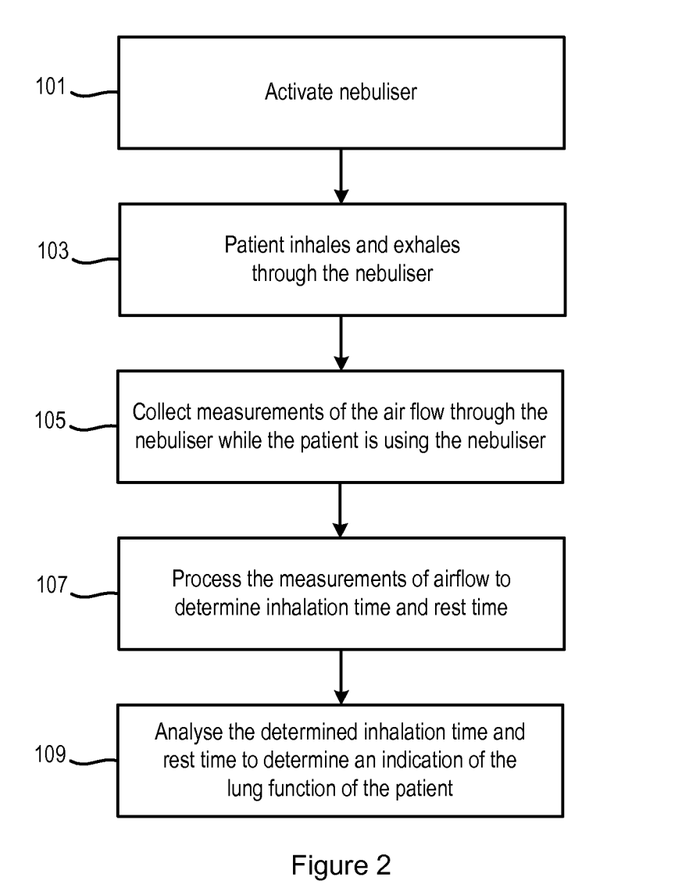
FIG. 2 is a flow chart illustrating a method of monitoring the lung function of a patient according to an embodiment of the invention.

A method of determining and monitoring the lung function of a patient according to an embodiment of the invention is shown in FIG. 2. In the first step, step 101, which occurs when the patient is going to use the nebulizer 2 to administer a dose of medication, the nebulizer 2 is filled with the required dosage of medication and the nebulizer 2 is activated.

In step 103, the patient inhales and exhales through the nebulizer 2. As the patient inhales, the air flow sensor 13 in the nebulizer 2 detects the flow of air through the nebulizer 2 in the direction of the patient, and the control unit 22 controls the actuator 14 to nebulize the liquid 12. The control unit 22 controls the actuator 14 to stop nebulizing the liquid 12 when the measurements from the air flow sensor 13 indicate that the patient has stopped inhaling (or in some cases shortly before a predicted end of the inhalation), and is either holding their breath (for example to maximize the time in which the nebulized liquid is present in their lungs, which is indicated by a generally zero air flow through the nebulizer 2) or exhaling (which is indicated by the air flowing through the nebulizer 2 from the patient towards the air inlet 6.

While the patient is inhaling and exhaling through the nebulizer 2, the control unit 22 collects and stores the measurements of the direction of the air flow through the nebulizer 2 (step 105).

Steps 103 and 105 occur until the required amount of liquid 12 has been nebulized (which could, for example, be measured in terms of the actuation time of the nebulizer 2, or by a measurement of the amount of liquid 12 remaining in the nebulizer 2—those skilled in the art will be aware of other techniques for determining when a treatment dose has been completed).

In some cases, the patient can be required to perform tidal breathing while using the nebulizer 2 (i.e. the patient is inhaling and exhaling normally while they are at rest).

In some other cases, the nebulizer 2 may be configured to operate in accordance with a target inhalation mode (TIM) of operation in which the patient is encouraged to inhale for as long as they can. In nebulizers operating under a target inhalation mode that have a maximum actuation time (e.g. 7 seconds), the patient will be encouraged to inhale up to or just beyond this maximum actuation time (e.g. 8 seconds). The target inhalation mode of operation can result in a greater amount of the liquid 12 getting into the lungs, and can also reduce the treatment time. In a target inhalation mode, the patient has to breathe in through the nebulizer 2 for a required amount of time from the start of the breath called the target inhalation time (i.e. how long the patient should inhale). The patient can be notified that the target inhalation time for a particular breath has been reached, for example, by the nebulizer 2 emitting a noise or by the mouthpiece portion at air outlet 8 vibrating. Preferably, in the target inhalation mode, the target inhalation time increases with each successful inhalation (i.e. an inhalation that passes the target inhalation time). For example, at the beginning of the treatment, the target inhalation time can be set to 3 seconds. If the patient is able to inhale past the target inhalation time, then the target inhalation time for the next breath is made a little longer. In this way, the duration of the breath is gradually increased until the patient reaches a target inhalation time that is suited to his/her own capabilities. If the patient is not able to inhale past the target inhalation time, then the target inhalation time for the next breath can be maintained at the current level or made a little shorter. If the nebulizer 2 operates in accordance with a target inhalation mode in steps 101-103, the control unit 22 can store information on the target inhalation time or times set for the patient for each breath. This information can then be used by the control unit 22 or remote terminal 3 in determining the indication of the lung function of the patient.

Once a particular treatment (i.e. administration of a dose of medication) has been completed, the measurements collected from the air flow sensor 13 are processed to determine the inhalation time and/or rest time of the patient during the treatment (step 107). As described above, this processing can be performed by the control unit 22 in the nebulizer 2 or by the remote terminal 3 after the measurements have been transferred to the remote unit 3 from the nebulizer 2. The processing of the measurements to determine the inhalation time and/or rest time is described below with reference to FIG. 3.

Figure 3:
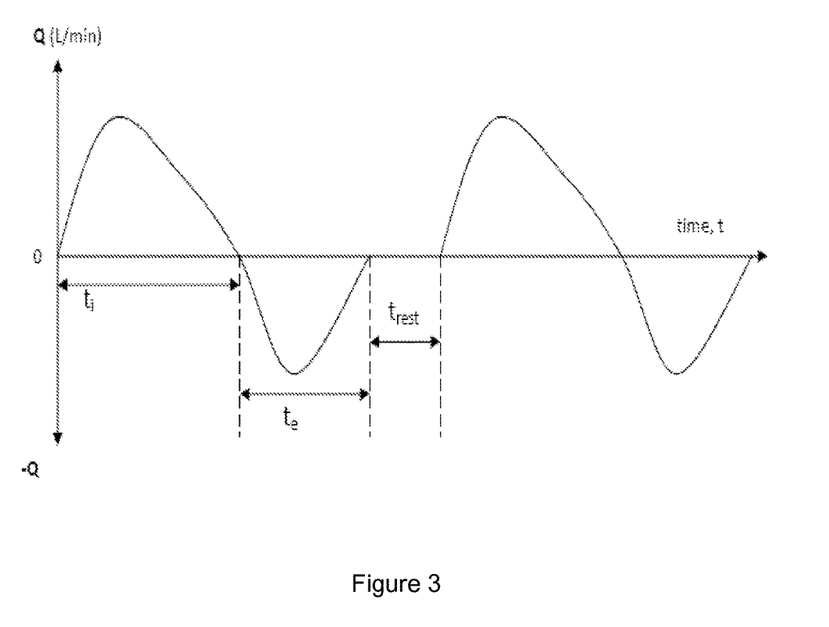
FIG. 3 is a graph illustrating the inhalation time and rest time measured in embodiments of the invention.

FIG. 3 is a graph in which the measurements from the air flow sensor 13 (shown in terms of volume flow Q—liters/minute) for a portion of a treatment are plotted against time. Positive values of Q represent inhalations, and negative values of Q represent exhalations.

The duration of each inhalation, the inhalation time corresponds to the time from the start of an inhalation (i.e. when Q becomes a positive value) to the end of that inhalation (i.e. when Q next becomes 0 or a negative value). The duration of each exhalation, the exhalation time $t_e$, corresponds to the time from the start of an exhalation (i.e. when Q becomes a negative value) to the end of that exhalation (i.e. when Q next becomes 0 or a positive value). Nominally, the duration of a rest period $t_{rest}$ corresponds to the time from the end of an exhalation to the start of the next inhalation (i.e. the period where Q is zero), as illustrated in FIG. 3. Although unlikely to occur mid-inhalation or mid-exhalation, any periods where the flow is zero count towards the duration of the rest period. Alternatively, periods of zero flow due to the patient holding their breath after inhaling can be omitted from the calculated rest period.

The duration of the rest period $t_{rest}$ can be determined directly by evaluating the time between the end of an exhalation to the start of the next inhalation, or indirectly by determining the time between the start of consecutive inhalations and subtracting the inhalation time $t_i$ and the exhalation time $t_e$.

In addition to determining the inhalation time $t_i$, exhalation time $t_e$ and/or the rest time $t_{rest}$ for one or more breaths in a treatment, it is possible to determine the total time spent inhaling, TSI, during a treatment (i.e. administration of a complete dose of medication), the total time spent exhaling, TSE, during the treatment and/or the total time spent resting, TSR, during the treatment.

The total time spent inhaling TSI is given by $$TSI = \sum_{j=1}^{N} t_{ij} \quad (1)$$

where N is the number of breaths through the nebulizer 2 required to complete the treatment and $t_{ij}$ is the inhalation time for the j-th breath in the treatment.

The total time spent exhaling TSE is given by $$TSE = \sum_{j=1}^{N} t_{ej} \quad (2)$$

where N is the number of breaths through the nebulizer 2 required to complete the treatment and $t_{ej}$ is the exhalation time for the j-th breath in the treatment.

The total time spent resting TSR can be given by $$TSR = TT - (TSI + TSE) \quad (3)$$

where TT is the time from the start of the first inhalation in the treatment to the end of the last exhalation in the treatment. It will be appreciated by those skilled in the art that the total time spent resting TSR can alternatively be determined directly by summing the durations of each detected rest period.

In addition to the above, or as an alternative, it is possible to calculate the average inhalation time, exhalation time and/or rest time for the breaths in a treatment. These averages can be calculated by dividing the TSI, TSE and TSR determined according to equations (1)-(3) above by the number of breaths, N.

Returning to FIG. 2, once the inhalation time and/or rest time (and optionally the total time spent inhaling and/or total time spent resting) have been determined, they are analyzed to determine an indication of the lung function of the patient (step 109). The indication of the lung function of the patient can be output to the patient via a display in the nebulizer 2 or by the remote terminal 3, along with an alert or warning, if appropriate. In addition, or alternatively, the indication of the lung function of the patient can be provided to a healthcare professional for the patient, preferably along with previous values for the indication, so the healthcare professional can assess the current condition of the patient.

The patient's lung function can be broadly assessed in terms of the effect the function of the lungs has on the patient's performance in using the nebulizer 2. For example, in a target inhalation mode of operation where the patient is required to breathe slowly and deeply, short inhalations and frequent and significant rest periods are a strong indication of poor lung function as they show that the patient is struggling to complete the breathing manoeuvre.

The analysis in step 109 can take a number of forms. For example, in a simple embodiment, a threshold can be set for each of the inhalation time and rest time (or for the total inhalation time and total rest time, or average inhalation time and average rest time, as appropriate). In this case, if the inhalation time falls below the inhalation time threshold (indicating the inhalation is too short) and/or the rest time exceeds the rest time threshold (indicating the rest period is too long), then the output of the method can be an indication that the patient's lung function is poor/unsatisfactory. Alternatively, respective thresholds can be applied to the TSI and/or TSR (or the average inhalation time and/or rest period). It will be appreciated that multiple thresholds can be set for the inhalation time and/or rest time which provides a finer level of granularity in the assessment of the lung function of the patient.

In another embodiment, the inhalation time and/or rest time can be compared to the inhalation time and/or rest time from one or more previous treatments. A shortening of the inhalation time and/or an increase in the rest time can indicate that the patient's lung function has deteriorated, and vice versa. Alternatively, the change in inhalation time and/or rest time can be compared to one or more thresholds to determine the extent to which the patient's lung function has changed. If the time that has elapsed between treatments has been recorded by the nebulizer 2 (or can be derived from a stored time of each treatment), the rate of change in the inhalation time and/or rest time can be determined. Again, the determined rate of change in the inhalation time and/or rest time can be compared to one or more thresholds to determine the significance to the lung function of the patient. A rapid reduction in the inhalation time and/or a rapid increase in the rest period can indicate a significant deterioration in the lung function of the patient, which can lead to an alert or warning message being issued by the nebulizer 2 or remote terminal 3 to the patient. It will be appreciated that the analysis described in this paragraph can alternatively be performed using the average inhalation time and average rest time, or the total inhalation time and total rest time.

In a preferred embodiment, the inhalation time and rest time can be combined to give a 'lung function index' (LFI) in the form $$LFI = \frac{TSI}{TSR + c} \quad (4)$$

where c is a constant having a non-zero value (which is provided to ensure that the denominator in equation (4) is non-zero, since it is not uncommon for patients not to rest at all). c can, for example, be 1. The lung function index in equation (4) has a maximal value when inhalation times are short and rest times are long. Alternatively, the LFI can be calculated for one or more inhalations and the associated rest time (i.e. LFI=$t_i/(t_{rest}+c)$), or it can be calculated from the average inhalation time and average rest time.

Alternatively, the inhalation time and rest time can be combined to give a 'lung deterioration index' (LDI) which is the reciprocal of equation (4) with c=0:

$$LDI = \frac{TSR}{TSI} \quad (5)$$

which has a maximal value when inhalation times are short and rest times are long. As with the lung function index above, the LDI can be calculated for one or more inhalations and the associated rest time (i.e. LDI=$t_{rest}/t_i$), or it can be calculated from the average inhalation time and average rest time.

Another preferred metric is the proportion of the total treatment time spent resting, which can be given, in percentage form, by:

$$\text{Resting\_fraction} = \frac{TSR}{TT} * 100\% \quad (6)$$

The lung function index and/or resting_fraction indicated above can be compared to respective threshold values, or previously-obtained values of the lung function index and resting_fraction to determine the current lung function of the patient.

The values for any of the thresholds described above can be set based on a typical or average user of the nebulizer 2, or alternatively the threshold(s) can be set specifically for the patient based on their medical condition using values for the inhalation time and rest time obtained during a test procedure during which the patient's lung function is deemed to be normal or abnormal (for that particular patient). In that case, it will be appreciated that instead of comparing the determined inhalation time and/or rest time to thresholds, the determined inhalation time and/or rest time can be compared to the base-line values for the patient.

As an example, a patient with good lung function might typically only rest for a total of 10 seconds during a whole treatment, and they might inhale slowly to achieve an 'ideal' mean inhalation of 8 seconds for each breath. This patient might take 9 breaths to inhale 0.5 ml of nebulized liquid when the nebulizer 2 is operating according to a TIM manoeuvre and the patient is inhaling for 8 seconds each time (with the output rate of the nebulizer 2 when actuated being 0.5 ml/min). Conversely, a patient struggling with the breathing manoeuvre (through poor lung function or poor technique) may only have short mean inhalation time of 0.6 seconds whilst resting for 360 seconds (6 minutes) across the whole treatment. This patient might require 200 breaths of 0.6 seconds to inhale 0.5 ml of nebulized liquid (when the nebulizer 2 switches off the actuator halfway through each breath to increase the residence time of the nebulized liquid in the lungs of the patient).

A typical threshold for the inhalation time or mean inhalation time could therefore be 1 second, and a typical threshold time for the total rest time could be 120 seconds. An alert could be issued where the mean inhalation time is less than 1 second and where the rest time is greater than 120 seconds.

Where the resting_fraction is determined according to equation (6) above, a threshold of 1 second can be applied to the mean inhalation time and a threshold of 40% applied to the resting_fraction. An alert could be issued where the mean inhalation time is less than 1 second and where the resting_fraction is greater than 40%.

For the lung function index given in equation (4), the healthy patient above will have an LFI of 6.54 (with c=1), the poorly patient having an LFI of 0.33 (again with c=1).

LFI=TSI/(TSR+1)=72/11=6.54　　　　Healthy lungs:

LFI=TSI/(TSR+1)=120/361=0.33　　　　Poorly lungs:

In some cases, particularly where the initial breaths by the patient are much shorter than the rest of the breaths during a treatment (for example where the TIM sets the initial target inhalation time at a low value but the performance of the patient means that it rapidly increases to the maximum target value) it is possible to discard the inhalation times and any rest time associated with those initial breaths from the calculation of the lung function in order to avoid those shorter breaths from influencing the result of the lung function calculation.

It will be appreciated that the indications of the lung function can be presented to the patient or healthcare professional in a number of different ways. As indicated above, the nebulizer 2 or remote terminal 3 can present a specific indication to the patient or healthcare professional once it has been determined (for example using a display on the nebulizer 2 or remote terminal 3). The indication can be presented in terms of a simple 'satisfactory/unsatisfactory' or 'improving/deteriorating' indication, or as a graph or chart showing the changes in lung function over time. This can allow a patient or healthcare professional to more easily identify any longer term trend in the lung function of the patient.

Thus, there is provided an improved method and system for determining an indication of the lung function of the patient. In particular, the indication of the lung function is readily derivable from parameters that are obtainable from an apparatus that can used in the home environment of a patient. The invention can also provide an early indication of when the lung function of the patient may significantly deteriorate.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of detecting a pulmonary exacerbation in a patient, the method comprising:

measuring, with a respiratory apparatus configured to deliver medication to a patient, a first inhalation time and a first rest time for the patient during a first medication treatment, wherein inhalation time is the amount of time for which the patient inhales through the respiratory apparatus, and rest time is the amount of time between the end of an exhalation and the start of a next inhalation during a medication treatment;

determining, with the respiratory apparatus, a first lung function index based on the first inhalation time and the first rest time, wherein the first lung function index is a ratio of the first inhalation time to the first rest time;

measuring, with the respiratory apparatus, a second inhalation time and a second rest time for the patient during a second medication treatment;

determining, with the respiratory apparatus, a second lung function index based on the second inhalation time and the second rest time, wherein the second lung function index is a ratio of the second inhalation time to the second rest time;

calculating, with the respiratory apparatus, a change in a lung function of the patient based on a comparison between the second lung function index and the first lung function index;

generating, with the respiratory apparatus, an indication that the patient is experiencing a pulmonary exacerbation responsive to the change in the lung function satisfying a change threshold; and presenting, on a display of the respiratory apparatus, the indication that the patient is experiencing a pulmonary exacerbation.

2. A method as claimed in claim 1, further comprising sending, with the respiratory apparatus, the indication that the patient is experiencing a pulmonary exacerbation to a remote computer system over the Internet.

3. A method as claimed in claim 1, wherein the method further comprises: determining a target inhalation time, wherein the patient is required to inhale through the respiratory apparatus for the target inhalation time.

4. A method as claimed in claim 3, wherein the method further comprises increasing the target inhalation time for a subsequent inhalation by the patient responsive to the patient inhaling for a time equal to or exceeding the target inhalation time.

5. A method as claimed in claim 1, wherein the inhalation time is one or more of: the amount of time for which the patient inhales through the respiratory apparatus in a single breath, the average amount of time for which the patient inhales through the respiratory apparatus over a plurality of breaths, and the total amount of time that the patient is inhaling through the respiratory apparatus over a plurality of breaths.

6. A method as claimed in claim 1, wherein the rest time is one or more of: the amount of time between the end of an exhalation and the start of the next inhalation for a single breath, the average amount of time between the end of an exhalation and the start of the next inhalation over a plurality of breaths, and the total amount of time between the end of an exhalation and the start of the next inhalation over a plurality of breaths.

7. A method as claimed in claim 1, wherein the method further comprises determining a rate of change in the lung function of the patient.

8. A method as claimed in claim 7, wherein the method further comprises comparing the determined rate of change in the lung function of the patient to one or more rate of change thresholds.

9. A computer-readable non-transitory storage medium containing instructions that when executed by one or more processors of a respiratory apparatus configured for delivering medication to a patient and detecting a pulmonary exacerbation in a patient, cause the one or more processors to perform the steps of:

measuring a first inhalation time and a first rest time for the a patient during a first time period in which the respiratory apparatus is delivering a first medication treatment to the patient, wherein inhalation time is the amount of time for which the patient inhales through the respiratory apparatus, and rest time is the amount of time between the end of an exhalation and the start of a next inhalation during a medication treatment;

determining a first lung function index based on the first inhalation time and the first rest time, wherein the first lung function index is a ratio of the first inhalation time to the first rest time;

measuring a second inhalation time and a second rest time for the patient during a second time period in which the respiratory apparatus is delivering a second medication treatment to the patient;

determining a second lung function index based on the second inhalation time and the second rest time, wherein the second lung function index is a ratio of the second inhalation time to the second rest time;

calculating a change in a lung function of the patient based on a comparison between the second lung function index and the first lung function index;

generating an indication that the patient is experiencing a pulmonary exacerbation responsive to the change in the lung function satisfying a change threshold; and presenting, on a display of the respiratory apparatus, the indication that the patient is experiencing a pulmonary exacerbation.

10. A respiratory apparatus for delivering medication to a patient and detecting a pulmonary exacerbation in the patient, the respiratory apparatus configured to:

deliver medication to a patient;

measure an a first inhalation time and a first rest time for the patient during a first time period in which the respiratory apparatus is delivering a first medication treatment to the patient, wherein inhalation time is the amount of time for which the patient inhales through the respiratory apparatus, and rest time is the amount of time between the end of an exhalation and the start of a next inhalation during a medication treatment;

determine a first lung function index based on the first inhalation time and the first rest time, wherein the first lung function index is a ratio of the first inhalation time to the first rest time;

measure a second inhalation time and a second rest time for the patient during a second time period in which the respiratory apparatus is delivering a second medication treatment to the patient;

determine a second lung function index based on the second inhalation time and the second rest time, wherein the second lung function index is a ratio of the second inhalation time to the second rest time;

calculate a change in a lung function of the patient based on a comparison between the second lung function index and the first lung function index;

generate an indication that the patient is experiencing a pulmonary exacerbation responsive to the change in the lung function satisfying a change threshold; and present, on a display of the respiratory apparatus, the indication that the patient is experiencing a pulmonary exacerbation.

\* \* \* \* \*